United States Patent [19]

Fernandez-Larsson

[11] Patent Number: 5,851,758
[45] Date of Patent: Dec. 22, 1998

[54] CYTOPATHIC REPLICATION OF HEPATITIS C VIRUS IN A NEW CELL LINE

[75] Inventor: Roberto P. Fernandez-Larsson, Silver Spring, Md.

[73] Assignee: Childrens Research Institute, Washington, D.C.

[21] Appl. No.: 547,842

[22] Filed: Oct. 25, 1995

[51] Int. Cl.$^6$ .............. C12Q 1/70; G01N 33/53; C12N 5/22; A61K 39/42
[52] U.S. Cl. .............. 435/5; 435/7.1; 435/40.51; 435/372; 435/372.3; 424/161.1; 530/826
[58] Field of Search ............... 435/5, 7.1, 40.51, 435/240.1, 240.2; 424/161.1; 530/824

[56] References Cited

FOREIGN PATENT DOCUMENTS

| 0 318 216 A1 | 5/1989 | European Pat. Off. |
| 0 414 475 A1 | 2/1991 | European Pat. Off. |
| WO 90/10060 | 9/1990 | WIPO . |
| WO 94/25064 | 11/1994 | WIPO . |

OTHER PUBLICATIONS

Popovic et al. Lancet 2 Dec. 1984 1472–73.
Somasundaran et al. J Virology Oct. 1987 61 (10) 3114–9.
Tersmette et al. J Virology Jun. 1988 62 (6) 2026–32.
Sei et al. Cellular Immunol. Jan. 1990 125 (1) 1–13.
Maul et al. J Virology May 1988 62 (5) 1768–73.
Zignego et al. J Hepatology Jul. 1994 15:382–86.
Shimizu et al., "Evidence for in vitro replication of hepatitis C virus genome in a human T–cell line", *Proc. Natl. Acad. Sci.*, 89:5477–5784, Jun. 1992.
Shimizu et al., "Correlation between the infectivity of hepatitis C virus in vivo and its infectivity in vitro", *Proc. Natl. Acad. Sci.*, 90:6037–6041, Jul. 1993.
Jacob et al., Expression of Infectious Viral Particles by Primary Chimpanzee Hepatocytes Isolated during . . . , *Jnl. of Infect. Dis.*, 161:1121–1127, 1990.
Nissen et al., "In vitro replication of hepatitis C virus in a human lymphoid cell line (H9)", *Jnl. of Hepatology*, 20:437, 1994.

*Primary Examiner*—Michael P. Woodward
*Assistant Examiner*—Mary K. Zeman
*Attorney, Agent, or Firm*—Foley & Lardner

[57] ABSTRACT

We have cloned human lymphoid cell lines that are susceptible to hepatitis C virus (HCV) infection, and in which infection with HCV results in the development of cytopathic effects, including cell degeneration, induction of cell syncytia and cell death, as well as in the production of progeny virus. Infection was confirmed by the polymerase chain reaction, indirect immunofluorescence of viral antigens, and detection of the viral RNA-dependent RNA polymerase. Progeny virus released from the infected cells into the medium could be serially passaged using the cell-free supernatant fluid as the inoculum. Also described are uses of the cloned cell lines for both intact cell and cell-free assay systems for the effectiveness of candidate anti-HCV drugs.

10 Claims, 2 Drawing Sheets

CYTOPATHIC REPLICATION OF HEPATITIS C VIRUS IN A NEW CELL LINE

BACKGROUND OF THE INVENTION

The field of the invention is, in general, cell lines for the replication of hepatitis C virus (HCV). More particularly, the invention relates to new cloned human cell lines in which infection by HCV is cytopathic, and provides for the first time an in vitro model of the in vivo disease.

The hepatitis C virus (HCV) is a recently identified, enveloped, single-stranded positive RNA virus. It is a member of the Flaviviridae family, has been classified as a new genus distinct from the flavivirus and pestivirus genera. Infection with this virus can result in various clinical outcomes, including acute and chronic hepatitis, and eventually end-stage liver disease, cirrhosis, and hepatocellular carcinoma. The 9.4 kb positive-strand genome contains one large open reading frame capable of encoding a polyprotein of 3010/3011 amino acids. Sequence comparisons, indicate that the HCV genome is most closely related to those of the pesti- and flavi-viruses, which also contain a similarly organized genome encoding a large polyprotein that is subsequently cleaved into mature viral proteins by a combination of host and viral-encoded proteases Current understanding of the life cycle of this virus is based largely on inference from its genomic sequence, the deduced structure of the single encoded polyprotein, and knowledge gained from other viral systems.

Despite the progress in understanding the molecular biology of HCV, many characteristics of the virus remain obscure, presumably because of the lack of suitable biological systems in which to study the effects of the virus. To date, several cell culture systems have been reported in which HCV can be propagated, including established cell lines (see, Nissen et al., *J. Hepatol.* 20: 437 (1994); WO 94/25064; EP O 414 475; WO 90/10060; Shimizu et al., PNAS USA 89:5477 (1992); Kato et al. *Biochem. Biophys. Res. Commun.* 206:863 (1995); Shimizu et al. *Proc. Natl. Acad. Sci. USA* 90:6037–6041 (1993)) and primary cell cultures (see, Jacob et al. *J. Infect. Dis.*161:1121 (1990); Carloni et al., *Arch. Virol.* [Suppl] 8:31 (1993); Lanford et al., *Virology* 202:606 (1994)).

Although full-cycle replication has been shown by serial passage, detection of viral infection has usually been limited to reverse transcription-polymerase chain reaction of positive and negative sense HCV RNAs. In short, no cell culture system has been reported in which the virus actually produces cytopathic effects similar to those observed in vivo. Therefore, there remains an important need for in vitro infectivity and viral neutralization assays in cell lines in which the virus not only propagates, but is cytopathic as well. In the absence of a cell culture model system in which to investigate differences in neutralization and cytopathic effects of HCV, nucleotide sequence comparisons have become the principal techniques for characterizing distinct variants of HCV (see, e.g., Bukh et al., *PNAS USA* 91:8239 (1994); Hino et al.,*J. Med. Virol.* 42:299 (1994); Simmonds, *Hepatology* 21:570 (1995); Stuyver et al., *PNAS USA* 91:10134 (2994)) Indeed, classification of HCV into genotypes has become one of the strongest areas of HCV research. The correlation between the defined genotypes and cytopathic and serological variants would be of obvious importance.

It is therefore an object of this invention to provide established human cell lines that are susceptible to HCV infection and in which infection is followed both by viral replication and virus-induced cytopathic effects, such that the cell line can serve as an in vitro model of in vivo infection of humans by this virus.

It is another object of this invention to provide assays, using the aforementioned established cell lines, for the anti-HCV potency of new and known drugs.

SUMMARY OF THE INVENTION

This object has been achieved by the cloning of novel human lymphoid cell lines that are suceptible to HCV infection, and in which infection with the virus results in the development of cytopathic effects, including cell degeneration, induction of cell syncytia and cell death, as well as in the production of progeny virions. The development of such an in vitro propagation system for HCV is the most important tool necessary for research on the mechanisms of viral replication, the function of the various viral proteins, the virus receptor, the development of a vaccine, and the discovery and testing of potential antiviral agents.

This object has also been achieved by the development of two, related tests for the anti-HCV efficacy of a drug. In the first test, the effect of the drug on the cytopathic effects of the virus is determined in intact, viral-infected cloned human lymphoid cells of the invention. In the second test, the effect of the drug on the propagation of the virus is determined by measuring the effects of the drug on RNA-directed RNA polymerase activity in detergent-disrupted, cell-free extracts of virus-infected cloned human lymphoid cells of the invention; an inhibition by the drug of the enzyme activity is indirectly reflective of an anti-cytopathic effect.

DETAILED DESCRIPTION OF THE INVENTION

Figure 1A:
FIG. 1A shows a photomicrograph of control, uninfected CH-61 cells at day 3 post-infection (200×).

It has been found unexpectedly that the sub-cloning by limiting dilution [Clarke et al., (1994) Cloning, in Basic Cell Culture, a Practical Approach, ed., Davis, Oxford Univ. Press, N.Y. pp 223–242] of lymphoid cell lines such as, preferably, the H9 human lymphoid-derived T-cell line, may produce clones that not only are infectable by the HCV but also, after infection, exhibit the cytopathic effects of HCV such as are seen in vivo, for example, cell degeneration, induction of cell syncytia, and cell death, along with propagation of the virus. In this respect, therefore, the present cloned cell lines can serve as an in vitro model system for studies of HCV infectivity and to test potential anti-HCV drugs for efficacy.

Cell cultures

H9 cells are known to support limited HCV replication (Nissen et al., 1994 above). We have found that single-cell derived clones from the putative subset of HCV-susceptible cells can be isolated by standard techniques of limiting dilution (Clarke et al., 1994 above) from the parental H9 cell line. H9 human lymphoid cells are available from the ATCC, Rockville, Md. (cat. no. HTB 176).

Virus inoculation

Cell clones may be infected by resuspending exponentially growing cells with a pool of two to four PCR-confirmed sera derived from HCV positive patients or with cell-free supernatants of previously infected cultures. After incubation for at least 6 h at 37° C., the cells are washed and resuspended in growth media (e.g., RPMI1640, 10% fetal calf serum). The infected cells should be observed for several weeks observing for any cytopathic changes, and cell and supernatant samples should be taken at regular intervals.

RNA extraction and PCR analysis

Cells may be extracted to recover viral RNA and then tested for the presence of viral sequences using the reverse transcription (RT) polymerase chain reaction (PCR) protocols of Numata et al. *J. Med. Virol.* 41:120 (1993) and others. The standard primers used representing the conserved non-coding 5' end of the genome were:

RFL-1(SEQ ID NO:1): 5'AACTACTGTCTTCACGCAGAAAGC3' (sense) genome positions 40–63 (Genbank M86779)

RFL-2(SEQ ID NO:2): 5'CCCAACACTACTCGGCTAGCAG3' (antisense) genome positions 255–234 (Genbank M86779)

Primer RFL-2 (SEQ ID NO:2) may be used for the RT assay to detect positive sense RNA (genome) and RFL-1 (SEQ ID NO:1) for the RT assay to detect negative sense RNA (putative replicative form).

Indirect immunofluorescent antibody (IFA) assay

An IFA assay [Sandstrom et al., *Transfusion*, 25:308 (1985); Blumberg et al., *J. Clin. Microbiol.* 23:1072 (1986)] may be performed on cells that have been washed three times with phosphate buffered saline, dried on glass slides, and fixed with methanol. A suitable primary antibody consists of pooled heat-inactivated (56° C. for 1.5 h) HCV-positive patient sera. The pool from 5 patients is suitable for these purposes. The secondary antibody may consist of a commercial fluorescein isothiocyanate (FITC)-labeled anti-human Ig antibody.

Determination of cell death

Virus specific cell death in HCV-infected cultures may be determined by either the standard trypan blue exclusion test, or by a commercial non-radioactive cell proliferation assay similar to the MTT [3-(4,4-dimethyl) thiazol-2-yl-2,5-diphenyl tetrazolium bromide] assay (CellTiter 96™, Promega). The assay is a colorimetric method that measures the number of viable cells in a culture. It is run by adding solutions of a tetrazolium compound to cells in culture. The tetrazolium compound is bioreduced by cells into a formazan that is soluble in culture medium. The quantity of formazan product as measured by absorbance at 490 nm is directly proportional to the number of living cells in culture (Promega Technical Bulletin 169).

Use of cloned cells to test for anti-viral potency of drugs

The cloned cell lines produced according to this invention are uniquely valuable as a means of testing for the anti-HCV potency of candidate drugs, including anti-HCV monoclonal and polyclonal antibodies. Whole cell and cell-free viral neutralization assay systems are described below.

Whole cell test system

In this system, suspensions of the cloned cell lines of the invention are incubated with a candidate drug either prior to, concurrently with, or subsequent to addition to the cells of a source of HCV, as is described above. At suitable points post-infection, the aforementioned indicia of cytopathicity are determined and the drugs ranked as to anti-HCV potency. This method is particularly suitable for testing agents whose mechanism of action is thought to be hindrance of the entry of the virus into the cell, or for testing drugs that require an intact cellular structure for action.

Cell-free HCV neutralization assay

Another means of testing the potential of anti-HCV drugs is afforded by a cell-free system for in vitro measurement of RNA polymerase. The system is derived from cytoplasmic extracts of detergent-treated HCV-infected cloned cells produced according to the present invention. We have observed that such detergent-treated extracts exhibit RNA-dependent RNA polymerase activity (RDRP), and also exhibit poly(U)-primed poly(A) polymerase activity, indicating that the extracts may also initiate RNA chains de novo.

In an initial, preparatory step, cloned human lymphoid cells produced according to this invention (above) are infected with HCV by incubating a suspension of the cells in an inoculum containing HCV and serum. Extracts are prepared by treating infected cells at ice-bath temperature with a solution of a detergent, preferably lysolecithin (Sigma Chem. Co., St. Louis, Mo.), then centrifuging off particulate matter.

The polymerase reaction mixture employed was adapted from that of Banerjee, in Bishop, ed., Rhabdoviruses, vol. II, CRC Press, Boca Raton, Fla., 1981. It contains NaCl, Tris buffer pH 8.0, $MgCl_2$, dithiothreitol, RNAse inhibitor (recombinant RHasin, Promega), actinomycin, ATP, GTP, CTP, UTP and [$^{32}$P]UTP, and cytoplasmic extract. Different template/primer combinations may be used: we found convenient poly(A).oligo(U), poly(A).oligo(dT)$_{16}$, and 7.5 kb poly(A)-tailed RNA (BRL, Gaithersburg, Md.) with oligo (dT)$_{16}$ as primer. Oligo (U$_{15-30}$) was prepared according to Plotsch et al., *J. Virol.* 63:216 (1989) by alkaline hydrolysis of poly(U).

In vitro polymerase reactions may be stopped by spotting an aliquot on glass fiber filters, and then drying. Filters are washed with TCA and EtOH, and the incorporation of [32P]-UMP determined by LSC. To analyze reaction products, reactions may be stopped by addition of sodium dodecylsulfate (SDS). RNA is extracted with phenol:chloroform:isoamyl alcohol, precipitated with ethanol, and fractioned on polyacrylamide-urea denaturing gels or agarose-formaldehyde-MOPS gels (see examples below for details).

To test drugs with anti-viral potential with the cell-free assay system above, two approaches may be taken. In one, the test drug is placed in contact with intact cells prior to cell disruption as described above. In the other, the test drug, e.g., ribavirin (ICN) or a nucleotide or nucleoside analog, is placed directly in the cytoplasmic extract used in the in vitro assay described above.

The material that follows is merely to exemplify specific embodiments of the invention that are described more fully in the specification and appended claims.

EXAMPLE 1

Isolation of clones of HCV-susceptible cells by limiting dilution

Fresh, exponentially growing H9 cells [obtained through the AIDS Research Reagent Program, Division of AIDS, National Institutes of Health, Bethesda, Md. from Dr. Robert Gallo, or from the ATCC, Rockville Md., cat. no. HTB 176] were diluted and seeded in 96-well plates at a statistical average of 0.5 cells/well in 150 μl of growth medium. Growing clones were subsequently transferred to 24-well plates, and then to 25 cm² flasks for further expansion. With that strategy, approximately 60 clones of cells were isolated.

Some of the clones isolated had a different morphology than the parental H9 cells. Eight of the clones are listed, inter alia, in Table 2.

EXAMPLE 2

Infection of cloned cells with HCV

Cloned lymphoid cell lines were initially infected with patient sera, because of evidence that HCV might replicate in the patient's peripheral blood mononuclear cells (Muller et al., *J. Gen. Virol.* 74:669 (1993)). Cloned cells were infected by resuspending log phase cells with a pool of two to four sera derived from HCV positive (PCR-confirmed) patients. After incubation for 1 h at 37° C., the cells were washed and resuspended in growth media (RPMI 1640, 10% fetal calf serum). The cultures were followed for two weeks, observing for any cytopathic changes and taking cell and supernatant samples at regular intervals.

Cell samples were extracted to recover viral RNA and then tested for the presence of viral sequences using the (RT)-PCR protocols as described. Negative sense RNA were detectable in cells up to day 8 post-infection. On the other hand, genome sense RNA was detected at all times in the supernatants up to day 13 post-infection, and starting at day 8 postinfection in the cell extracts (Table 1).

TABLE 1

Detection of HCV sequences by PCR in infected cloned cells

| Day PI[a] | Negative strand | | Positive strand | |
|---|---|---|---|---|
| | Cells | Sup[b] | Cells | Sup |
| 1 | +/−[c] | − | − | ++ |
| 3 | +/− | − | − | ++ |
| 8 | +/− | − | + | ++ |
| 13 | − | − | ++ | ++ |

[a] Day postinfection.
[b] Cell-free supernatant fluids.
[c] Relative intensity of PCR products detected in ethidium bromide stained agarose gels: (−) none, (+/−) weak, (+) good, (++) strong.

EXAMPLE 3

Susceptibility of Cloned Cells to HCV

The individual clones of cells were seeded in 24-well plates after infection with pooled patient sera (all sera PCR-confirmed HCV positive) as above. Cultures were followed for two weeks, and samples of the infected cells and supernatants at regular intervals postinfection were collected for detection of HCV infection. Detection of HCV infection was done by:

1. Indirect immunofluorescent antibody (IFA) staining of infected cells.
2. PCR of viral RNA.

Pronounced cytopathic changes were noted in four clones, with more subtle changes in others. Changes included alterations in the general morphology of the cultures, induction of syncytia, and cell death. We isolated the four cell clones (CH6, CH9, CH14, and CH34) that demonstrated the most pronounced changes.

HCV-infected clones were checked with IFA assays for HCV and also for HIV. Results are shown in Table 2.

TABLE 2

IFA staining of infected cell clones

| Cell Clone | anti-HIV[a] | anti-HCV[b] |
|---|---|---|
| CH-6 | − | + |
| CH-9 | − | + |
| CH-14 | − | + |
| CH-34 | − | + |
| CH-61 | − | + |
| CH-62 | − | + |
| CH-63 | − | + |
| CH-64 | − | + |
| uninfected H9 | − | − |
| HIV-infected H9 (HIV control) | + | − |

[a] IFA using HIV+ pooled patient sera as primary antibody.
[b] IFA using HCV+ pooled patient sera as primary antibody.

EXAMPLE 4

Isolation of Additional Cell Clones

Figure 1B:
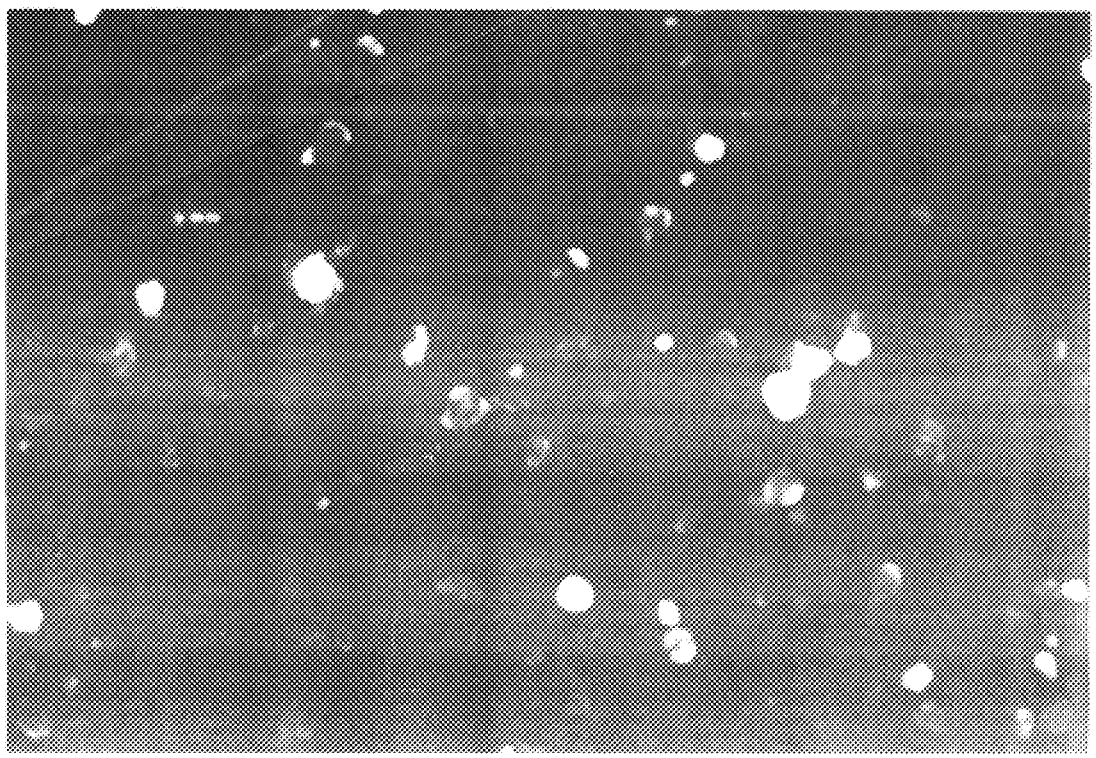
FIG. 1B is the corresponding photomicrograph for cells infected with HCV.
Figure 2A:
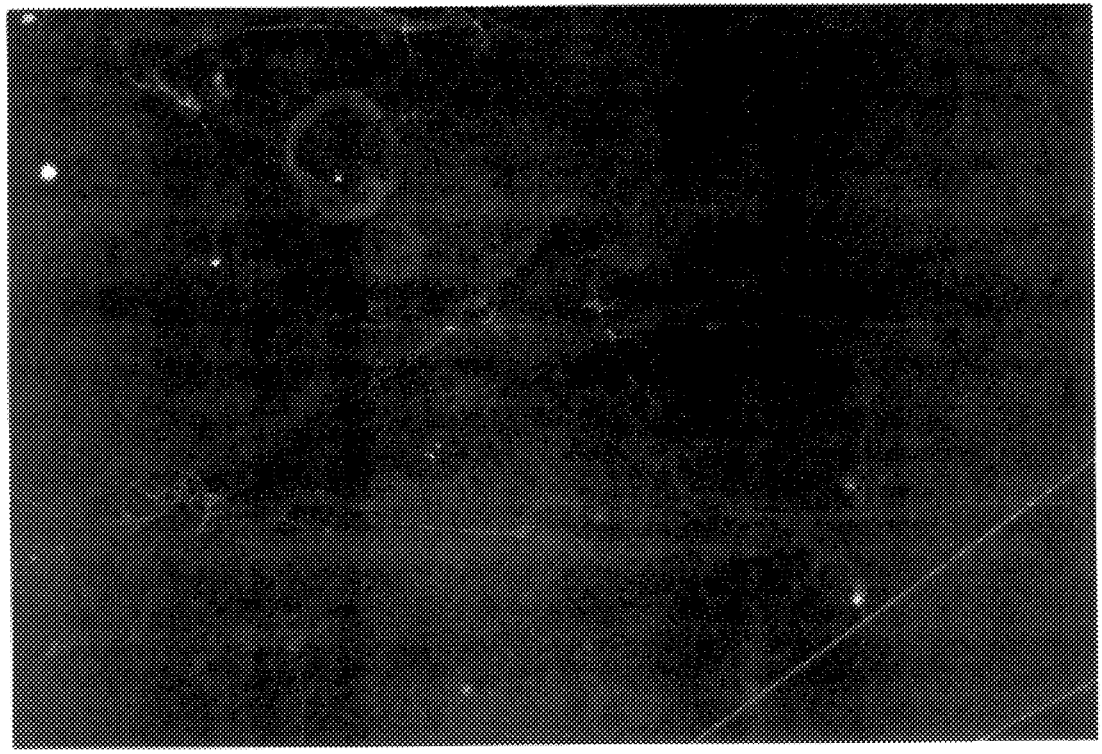
FIG. 2A shows a photomicrograph of control, uninfected CH-64 cells at 6 days post-infection (400×).
Figure 2B:
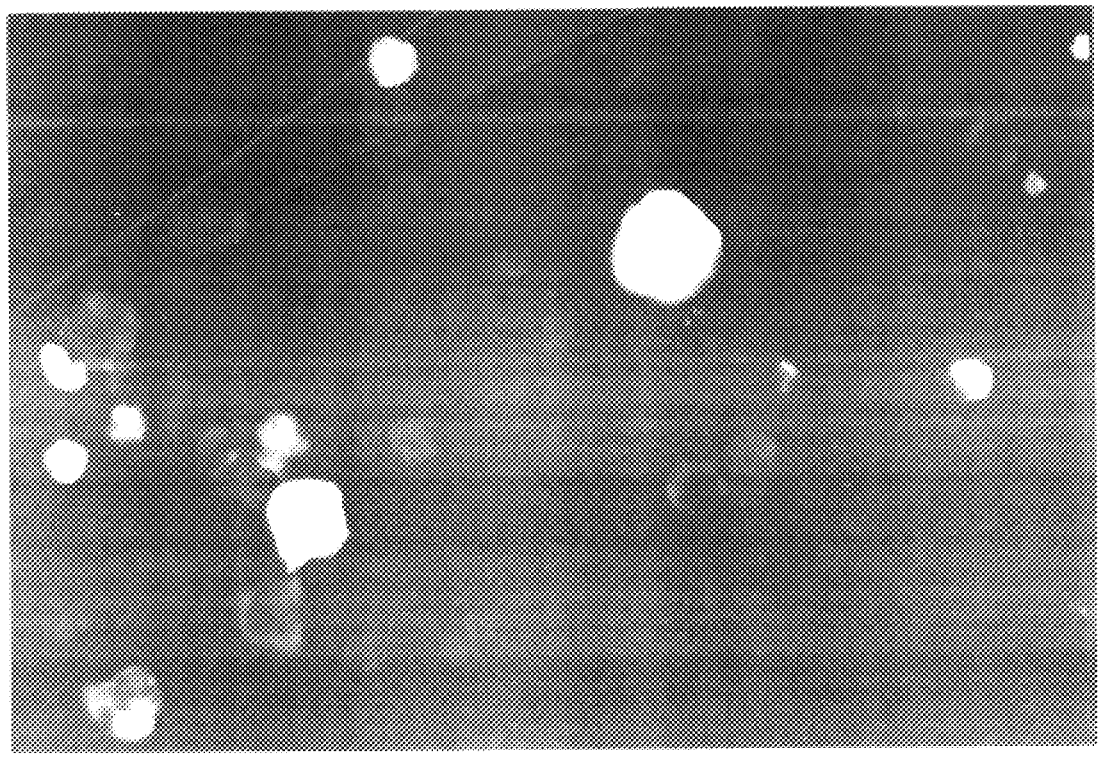
FIG. 2B is the corresponding photomicrograph for cells infected with HCV.

In a subsequent limiting dilution experiment another five cell clones (CH-61, CH-62, CH-63, CH-64, and CH-69) were isolated. In these clones, HCV infected a larger percentage of cells, as indicated by the IFA assays. FIG. 1 shows micrographs of HCV-infected (1B) and uninfected (1A) CH-61 cells at day 3 post-infection (200×). FIG. 2 shows HCV-infected (2B) and uninfected (2A) CH-64 cells at day 6 post-infection (400×). Scores of up to 30% infected cells were observed using the IFA assay in some cultures. Scoring of syncytia induction is less certain because certain of the cell clones show a natural propensity to form background syncytia. In addition, we believe that syncytia-induction might be a property of some HCV strains and not others, much in the same way as occurs with other enveloped RNA viruses.

In addition to the IFA assays, PCR analysis was performed on test cultures to confirm HCV infection. In order to confirm the negative IFA results for HIV, HIV p24 ELISA tests were run on supernatant fluids of infected cell clones. Results are shown in Table 3.

TABLE 3

HCV RT-PCR and HIV p24 ELISA assays of infected cell clones

| Cell Clone | HCV RT-PCR[a] | HIV p24 ELISA[b] |
|---|---|---|
| CH-6 | + | − |
| CH-9 | + | − |
| CH-14 | + | − |
| CH-34 | + | − |
| uninfected H9 | − | − |
| HIV-infected H9 | − | + |

[a] Specific PCR product detected in ethidium bromide-stained agarose gels.
[b] The lower limit of detection of this ELISA test is 12.5 pg/ml.

Virus specific cell death in HCV-infected cultures was assessed by two methods:

1. Trypan blue exclusion staining
2. A non-radioactive cell proliferation assay (CellTiter 96, Promega) similar to the MTT assay.

The best results, as far as the number of infected cells and the cell killing, were observed when the virus and the cells were incubated together for at least 6 hours. With incubation times of 1–3 hours; the levels of infection obtained at shorter periods were usable, although less satisfactory. It is possible that some HCVs might require long entry times. We have previously found, for example, that different HIVs can have 50% entry times (times required for 50% of the infectious particles to enter the cells) which ranged between less than 30 minutes to several hours, depending on the virus and the cell type (Srivastava et al., *J. Virol.* 65:3900 (1991)).

EXAMPLE 5
Virus-Specific Cell Death

The best results have been obtained with HCV stocks that have undergone passage in cells, rather than using patient serum as inocula. With such HCV stocks, close to 50% cell death have been observed for infected CH-69 cells at day 6 post-inoculation (Table 4). Cultures were also followed by IFA and by viral polymerase detection.

TABLE 4

Virus-specific cell death in CH-69 cells

| Day PI[a] | Passage[b] | % Dead[c] | % Formazan reduction[d] | IFA[e] | Viral polymerase assay[f] |
|---|---|---|---|---|---|
| 6 | 1 | 41 | 48 | + | ND[g] |
| 2 | 2 | 24 | 39 | + | ND |
| 5 | 2 | 24 | 27 | + | ND |
| 6 | 3 | 24 | ND | + | + |

[a]Days postinfection
[b]Number of the passage in cells
[c]As measured by the trypan blue exclusion assay
[d]As measured by the cell proliferation assay
[e]Detection of virus-specific antigens by IFA assay
[f]Detection of the viral polymerase in an in vitro transcription assay
[g]ND = not done

EXAMPLE 6
In Vitro RNA Synthesis

A suspension of log phase cloned human lymphoid cells produced according to the invention cells ($4 \times 10^6$) were resuspended in a 1 ml inoculum containing 0.5 ml HCV+ serum plus 0.5 ml RPMI. The cells were incubated for 6 h at 37° C., at which time RPMI medium with 10% fetal calf serum was added to dilute the cells to $1 \times 10^6$/ml. Every two days, the cells were counted and resuspended at $1 \times 10^6$/ml in fresh medium. Uninfected cultures were maintained similarly.

Cytoplasmic extracts from HCV-infected cells were prepared at 2, 4 and 6 days postinfection. Before feeding, $1 \times 10^6$ cells were removed from both infected and uninfected cultures. The cells were centrifuged at low speed to remove the supernatant and then washed twice in phosphate buffered saline. The cells were quickly resuspended in 15 µl of an ice-cold solution of L-lysophosphatidylcholine, palmitoyl (lysolecithin, Sigma) at 250 µg/ml for 1 minute on ice. The cells were gently disrupted by pipetting and centrifuged at full speed in a microfuge for 1 minute to pellet nuclei and cell debris. The cell-free supernatant was used in the polymerase assays after addition of a premix.

The polymerase reaction premixture (40 µl) described above contained a final concentration of 100 mM NaCl, 50 mM Tris HCl (pH 8.0), 5 mM $MgCl_2$, 4 mM DTT, 10 units RNase inhibitor, 4 µg/ml actinomycin C, 100 µM each ATP, GTP and CTP, 50 µM UTP, 10 µCi [$^{32}$P]UTP, and 10 µl cytoplasmic extract. Reaction mixtures were incubated at 30° C.

We used three different kinds of template/primer combinations: poly(A).oligo(U), poly(A).oligo(dT)$_{16}$ and 7.5 Kb poly(A)-tailed RNA.oligo(dT)$_{16}$. Oligo(U$_{15-30}$) was prepared as described above.

In vitro polymerase reactions were stopped by spotting an aliquot of each reaction on glass fiber filters and then drying. The filters were washed in 5% trichloroacetic acid and 95% ethanol, and [32P]-UMP incorporation counted in a toluene-based liquid scintillation cocktail.

To analyze the reaction products, the reactions were stopped by addition of SDS to 0.5%. RNAs were extracted with phenol:chloroform:isoamyl alcohol (50:49:1), precipitated with ethanol, and fractioned in 10% polyacrylamide-7M urea denaturing gels or 1% agarose-formaldehyde-MOPS gels.

Although detectable, there was limited [$^{32}$P]UMP incorporation in the cytoplasmic extract from infected cloned H9 cells without the addition of any exogenous template or primer. The addition of poly(A).oligo(dT)$_{16}$ to the reaction produced significant poly(U) polymerase activity (Table 5).

TABLE 5

Polymerase activity of HCV-infected cytoplasmic extracts from four cloned H9-derived cell lines

| Cytoplasmic extract: | Other additions | [$^{32}$P]-UMP incorporated (cpm) |
|---|---|---|
| 1. Uninfected | poly(A).oligo(dT)$_{16}$ | 0[a] |
| Infected (7 days PI)[b] | " | 4770 |
| 2. Uninfected | " | 0 |
| Infected (7 days PI) | " | 9782 |
| 3. Uninfected | " | 0 |
| Infected (7 days PI) | " | 4215 |
| 4. Uninfected | " | 0 |
| Infected (7 days PI) | " | 8867 |

[a]Background counts obtained from reactions with uninfected CE run concurrently were substracted from all other reactions.
[b]PI, postinfection.
1–4. Different cloned lines of lymphoid cells

What is claimed is:

1. A cloned human lymphoid T-cell line, obtained by subcloning H9 cells, wherein said clone exhibits a cytopathic effect upon infection with hepatitis C virus ("HCV"), wherein said cytopathic effect is selected from the group consisting of cell syncytia, cell degeneration and cell death.

2. A cloned cell line according to claim 1, wherein said cell line is the CH-69 clone.

3. A cloned cell line according to claim 1, wherein said cell line is the CH-34 clone.

4. A cloned cell line according to claim 1 wherein the RNA polymerase of said HCV is detectable and measurable after serial passage of cell-free virus stock obtained from the supernatant fluid of parental infected cultures.

5. A method of testing the anti-hepatitis C virus potency of a drug, comprising the steps of (a) contacting a cloned cell line of claim 1 with said drug either before, concurrently with, or after infection with hepatitis C virus, (b) infecting said cell line with hepatitis C virus, and (c) determining the cytopathic effect of said virus on said cells in the presence and absence of said drug.

6. A method of claim 5, wherein said drug is an anti-hepatitis C virus antibody.

7. A method according to claim 5, further comprising assaying for intracellular RNA-directed RNA polymerase activity, comprising the additional steps of: (a) disrupting said virus-infected cells with a detergent; (b) preparing a cytoplasmic extract from said disrupted cells; and (c) measuring said RNA polymerase activity of said cytoplasmic extract in the absence and presence of said drug, wherein said drug may optionally be placed in contact with said cells either before, during or after infection with said virus, or added directly to the cytoplasmic extract.

8. A method according to claim 7, further comprising adding a template and a primer to said cytoplasmic extract.

9. A method according to claim 8, wherein said template is poly(A) or 7.5 kb poly(A)-tailed RNA.

10. A method according to claim 8, wherein said primer is oligo(U) or oligo(dT)$_{16}$.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 24 base pairs (B) TYPE: nucleic acid
(C) STRANDEDNESS: single
(D) TOPOLOGY: linear (xi) SEQUENCE DESCRIPTION: SEQ ID NO:1:

AACTACTGTC TTCACGCAGA AAGC                    24

(2) INFORMATION FOR SEQ ID NO:2:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:2:

CCCAACACTA CTCGGCTAGC AG                      22